United States Patent [19]

Litzen et al.

[11] Patent Number: 4,762,616
[45] Date of Patent: Aug. 9, 1988

[54] ISOPROPYL ALCOHOL PURIFICATION PROCESS

[75] Inventors: David B. Litzen, Houston; Stephen R. Bolger, La Porte, both of Tex.

[73] Assignee: Shell Oil Company, Houston, Tex.

[21] Appl. No.: 943,356

[22] Filed: Dec. 19, 1986

[51] Int. Cl.$^4$ .............................................. B01D 11/04
[52] U.S. Cl. .................................................. 210/634
[58] Field of Search ........................ 210/634; 260/705; 568/889, 913, 918

[56] References Cited

U.S. PATENT DOCUMENTS

| | | | |
|---|---|---|---|
| 1,712,475 | 5/1929 | Buc | 260/705 |
| 2,510,806 | 6/1950 | Egberrs et al. | 260/705 |
| 2,994,720 | 8/1961 | Hakala et al. | 568/899 |

Primary Examiner—Frank Spear
Attorney, Agent, or Firm—Richard F. Lemuth

[57] ABSTRACT

A process for the purification of the crude isopropyl alcohol product of propylene hydration reactions. Crude isopropyl alcohol products, which comprise isopropyl alcohol, diisopropyl ether and polymeric impurities, are subjected to a specified sequence of multiple dilution and phase separation steps which serve to extract a substantial portion of the product's diisopropyl ether and polymeric impurities. The invention is particularly useful in removing odiferous sulfur-containing impurities from the products of indirect propylene hydration processes which involve the reaction of propylene with sulfuric acid to produce isopropyl sulfate followed by hydrolysis of the sulfate to isopropyl alcohol.

9 Claims, 1 Drawing Sheet

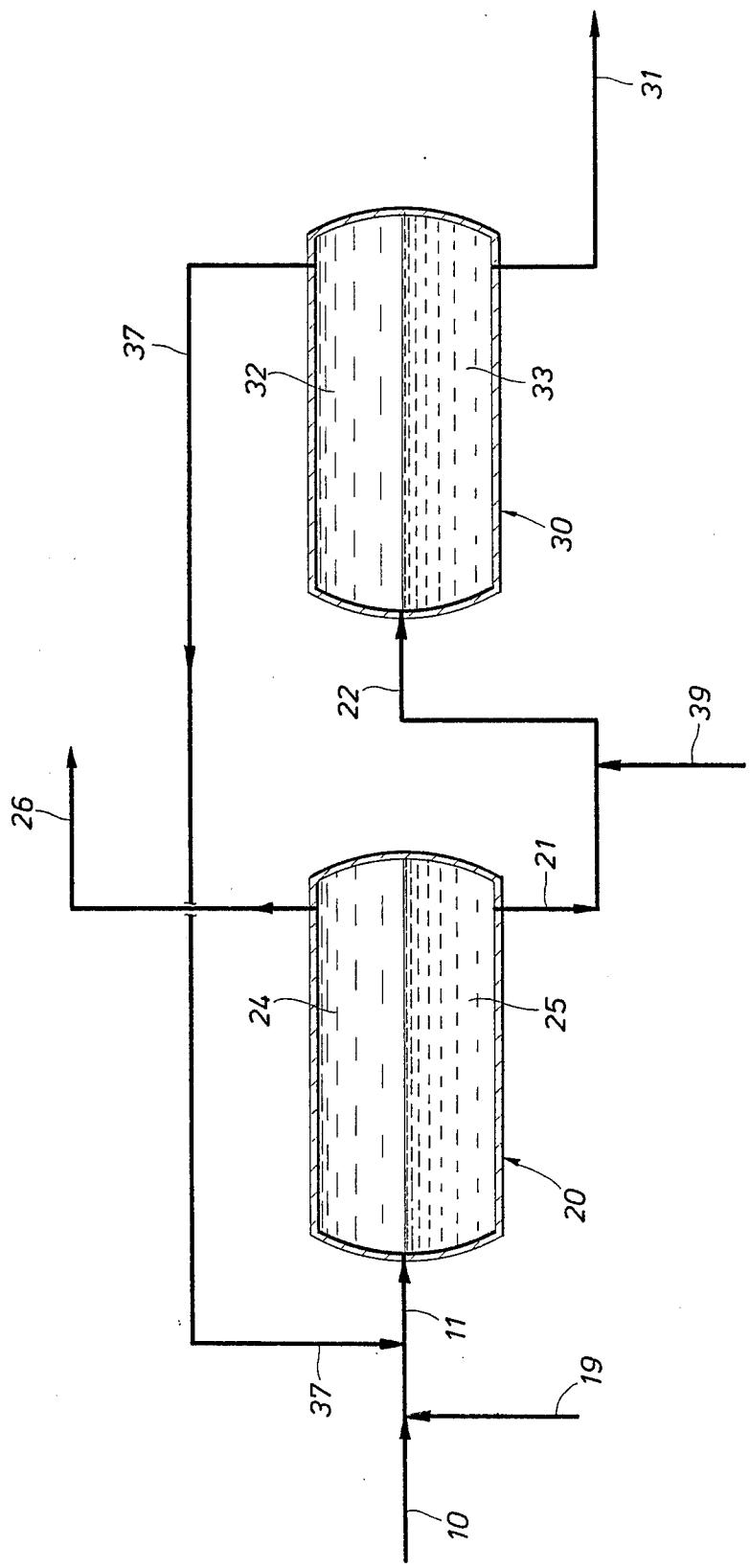

ISOPROPYL ALCOHOL PURIFICATION PROCESS

BACKGROUND OF THE INVENTION

This invention relates to an improved process for the purification of crude isopropyl alcohol.

Isopropyl alcohol (IPA) is well known to be conventionally manufactured by processes which involve the hydration of propylene. Hydration may be direct or indirect. In direct hydration, propylene is reacted catalytically with water. Suitable catalysts for this purpose are known to include cation exchange resins, concentrated phosphoric acid, silicotungstate compounds, etc.

The indirect hydration process, which is of particular interest in the application of the present invention, comprises steps for the reaction of propylene with sulfuric acid to produce propane sulfate followed by the hydrolysis of the sulfate to the desired IPA.

The crude product which results from propylene hydration processes typically contains not only the desired IPA but also diisopropyl ether, polymers (e.g., propylene trimers, tetramers, pentamers, etc.), and water. Organic sulfur derivatives are also found in the product of the indirect hydration process. In a typical operation the crude product might contain 60 percent by weight (% w) IPA, 6% w diisopropyl ether, up to 0.5% w of the polymers and sulfur derivatives, small amounts of acetone and propane, and the remainder water.

In conventional practice, the crude IPA from indirect propylene hydration to IPA is commonly treated for purification, or finishing, by distillation and/or extractive distillation to remove the diisopropyl ether and other impurities.

The principal object of this invention is improvement of crude IPA finishing. In one respect, it is particular object of the invention to reduce the difficulty and expense associated with operations applied in the prior art for the finishing of crude IPA. Conventional distillation practices have proven to be very costly both in terms of the necessary equipment and the energy required to operate it, e.g., energy necessary to vaporize not only the organic ether and IPA products but also the large content of water accompanying the IPA during finishing. For example, one typical prior art practice for purification of crude IPA involves feeding the crude stream from the propylene hydration to a multi-tray extractive distillation column, using a water extractant, to distill overhead most of the diisopropyl ether and other impurities, leaving a bottoms product containing about 15% IPA in water. This IPA solution is then subjected to multi-stage distillation to recover a distillation overhead consisting essentially of an azeotropic mixture of IPA and water. The IPA/water solution is then subjected to azeotropic distillation with an added azeotroping agent (for instance, finished isopropyl ether) for dehydration. Downstream of azeotropic distillation, remaining heavy components, including $C_6$ to $C_{12}$ polymers and diisopropyl ether, are rejected in a further multi-stage distillation.

In another respect, it is a particular object of the invention to improve the effectiveness of the removal of certain impurities from the crude IPA. In this respect, it is of particular interest to enhance the performance of the finishing process for the removal of organic sulfur derivatives from the product of the indirect hydration process. Even when present in only very small quantities, sulfur derivatives often impart a very undesirable odor to the finished IPA. Difficulties associated with sulfur removal may result in products which do not satisfy stringent specifications required for IPA in many end uses, e.g., its use in the formulation of cosmetic and pharmaceutical products.

SUMMARY OF THE INVENTION

The present invention provides a process for the purification of a crude isopropyl alcohol product of propylene hydration to remove diisopropyl ether, polymeric, and/or sulfur-containing impurities, which process comprises steps for:

(a) mixing the crude IPA product with the recycle stream from subsequent process step (f) and optionally with added water in the amount required to provide a mixture containing between about 73 and 83% w water, (b) in a first phase separation step, phase separating the mixture from step (a) into a first upper (nonpolar) phase rich in diisopropyl ether and a first lower (polar) phase rich in IPA and water, (c) withdrawing the first upper phase from the process, (d) admixing the first lower phase with added diisopropyl ether to obtain a mixture containing between about 10 and 21% w IPA, between about 1 and 4% w diisopropyl ether, and between about 77 and 87% w water, relative to the total weight of the resulting mixture, (e) in a second phase separation step, phase separating the mixture from step (d) into a second upper (nonpolar) phase rich in diisopropyl ether and a second lower (polar) phase rich in IPA and water, (f) recycling the second upper phase for use in dilution of the crude IPA in step (a), and (g) recovering the second lower phase as a purified IPA product.

In practice, the sequential phase separation steps of the invention function to reject from the crude IPA a substantial portion of its content of diisopropyl ether. Most importantly, the manner in which this ether is separated from the IPA serves to concentrate in the rejected ether a substantial portion of the crude IPA's content of polymeric and sulfur-containing impurities. The process concentrates these impurities in the withdrawn ether enriched product and accomplishes a significant purification of the IPA, by means other than distillation.

As a consequence of the practice of the invention, the aqueous IPA solution recovered from the process can be more readily finished to produce a high purity IPA product. Advantage can be realized from the invention in terms of savings in equipment and energy costs and/or in terms of preparing a higher quality, particularly a lower odor, IPA product.

BRIEF DESCRIPTION OF THE DRAWING

In a single FIGURE, the attached Drawing depicts a simplified schematic flow diagram of a preferred embodiment of the process according to the invention. Reference will be made to the FIGURE when this embodiment is described in greater detail in the Examples which follow.

DESCRIPTION OF THE PREFERRED EMBODIMENTS

In its broadest sense, the process according to this invention has application for the purification of any crude IPA product which contains both diisopropyl ether and polymeric impurities. The invention is particularly useful when applied to the treatment of a crude IPA which has been manufactured by the indirect hydration of propylene and which contains odiferous sulfur compounds. However, it can also be applied with substantial advantage in the finishing of the IPA product of direct hydration.

The invention is principally intended for application to the crude product of a hydration process. A typical crude IPA from conventional propylene hydration contains, for example, between about 40 and 70% w of IPA, about 1 to 10% w of diisopropyl ether, about 0.1 to 2% w of polymeric and/or sulfur-containing impurities, a small amount (e.g., 0.1 to 1% w of acetone) and the remainder (e.g., 20 to 55% w) water. Polymeric impurities are exemplified by propylene dimers, trimers, tetramers, pentamers, etc., as well as by addition products of propylene and such polymers of propylene with impurities found in other components introduced into the hydration reaction(s). It is often the case that the sulfur impurity in the product of indirect propylene hydration is largely found to be associated with such polymeric species. The relative proportions of the various components of crude IPA will vary somewhat, depending upon such factors as the source of the propylene feedstock and the nature of the hydration process. A crude IPA product containing about 55–60% w IPA, about 5% w diisopropyl ether, about 0.5% w polymeric and/or sulfur-containing impurities, about 0.5% w acetone, and about 40% w water would be considered very typical.

The invention can likewise be applied to a crude IPA stream, resulting from propylene hydration, which has been subjected to one or more preliminary purification steps, but which still contains significant quantities of diisopropyl ether (e.g., at least about 1% w, preferably at least about 2% w, and most preferably at least about 4% w).

For practice of the invention, the crude IPA together with added quantities of diisopropyl ether and water are processed through a sequence of steps, including multiple phase separations. The process can be conducted in either a continuous or batch mode. As a rule, continuous practice is preferred.

In a first step, the crude IPA product is mixed with a diisopropyl ether-enriched stream which is recycled from a subsequent point in the process during process step six described hereinbelow. The composition of the resulting mixture is further optionally adjusted in this first step, by addition of water if necessary, to provide a mixture containing between about 73 and 83% w water. Water addition is typically necessary to provide the specified concentration. However, water need not be added if the mixture of crude IPA and recycle streams contains sufficient water to bring its concentration in the mixture to the specified level. Preferably, the mixture prepared in this first step contains between about 14 and 20% w IPA, between about 2 and 8% w diisopropyl ether, and between about 75 and 81% w water. Particularly preferred is a mixture adjusted to contain between about 16 and 18% w IPA, between about 4 and 6% w diisopropyl ether, and between about 77 and 79% w water. The remainder of the mixture, typically about 1% w, comprises polymeric and/or sulfur-containing impurities, acetone, and possibly other impurities or by-products from the propylene hydration reactions.

The water added to the crude IPA in this first process step of the invention may be substantially pure water, or alternatively, may very suitably be a water-rich process stream from a source within the IPA production or finishing operation. Distillation steps in many conventional IPA finishing processes generate water-rich streams which are very suitable for use in this application. The added water need not be of high purity, and may contain, for example, quantities of IPA, isopropyl ether, polymers and the like.

In a second process step, this mixture from the first step is phase separated. This phase separation step is referred to as a first phase separation, in order to distinquish a second, subsequent, phase separation which is also a part of the process. In the course of this first phase separation, isopropyl ether concentrates in an upper phase while water and IPA concentrate in a lower phase. The first phase separation thus results in separation between a first upper (nonpolar) phase rich in diisopropyl ether and a first lower (polar) phase rich in IPA and water.

The upper, nonpolar phase resulting from this first phase separation step is enriched not only in diisopropyl ether but also in the polymeric and sulfur-containing impurities. In a third process step, this upper phase is withdrawn from the process. In effect, the invention functions to concentrate impurities in this phase, often to a concentration which can be ten-fold or more that of the crude IPA feed to the invention. If desired, the withdrawn upper phase can be further processed to recover IPA, and diisopropyl ether from the withdrawn phase, for instance, by conventional distillation or extractive distillation methods. Treatment of the relatively small amount of the withdrawn upper phase of the first phase separation to reject impurities present in relatively high concentration is much more practical and economical than distillation of the substantially larger crude IPA stream.

The fourth step of the invention comprises admixing of added diisopropyl ether with the lower (polar) phase of the first phase separation step (the second step of the overall process) to obtain a mixture containing between about 10 and 21% w IPA, between about 1 and 4% w diisopropyl ether, and between about 77 and 87% w water. The diisopropyl ether added to the IPA-rich lower phase during this step is preferably substantially free of polymeric and sulfur-containing impurities. Although the particular source of the added diisopropyl ether is not critical to the invention, it is often very convenient and generally preferred to recycle to this step diisopropyl ether which has been recovered by ether purification procedures which accompany the overall purification scheme, but are not a part of this invention. Recycling ether which has been purified from the crude ether withdrawn from the invention in the third step or from elsewhere in the IPA finishing operations is very convenient.

Following the addition and mixing of the diisoproypl ether into the lower phase of the first phase separation step, the resulting mixture is next subjected, in a fifth process step, to a second phase separation step, for separation of a (second) upper phase, from a (second) lower phase. As is also the case for the first phase separation step, the second upper phase is nonpolar in character and enriched in diisopropyl ether, polymers and sulfur-containing impurities, and the second lower phase is polar in character and enriched in IPA and water.

Each of the two phase separation steps carried out for purposes of the invention is suitably performed utilizing a separation vessel of generally conventional design. In a large-scale continuous process, for instance, the separations are very conveniently conducted in horizontal cylindrical vessels equipped with interface level control instrumentation. It is preferred in continuous operation that the phase separation vessel(s) provide an average residence time of at least ten minutes, calculated on the total flow of the liquid mixture into the vessel, in order for the phases to cleanly separate. Longer residence times, i.e., at least about 20 minutes and most particularly at least about 40 minutes, are considered preferred. Phase separations shorter than 10 minutes are suitable, although with some sacrifice in process efficiency.

In a sixth step of the invention, the second upper phase is recycled for use in the dilution of the crude IPA in the first step, as described above.

As a final, seventh, step in the process, the second lower phase resulting from the second phase separation is withdrawn as the desired purified IPA product.

Conditions of temperature and pressure for the various process streams, including IPA, diisopropyl ether, water, and other components and mixtures thereof are not narrowly critical to the practice of the invention. Preference can generally be expressed for operation at ambient or elevated temperatures, e.g., temperatures in the range from about 15° C. to 150° C., particularly in the range from about 50° to 110° C., to obtain rapid and complete phase separation in the two phase separation steps. However, very effective phase separation is realized at relatively lower temperatures with longer residence times. It is only in the two phase separation steps that temperature is significant to performance of the process. Suitable process pressures include those sufficiently high to maintain the process mixtures substantially in the liquid state. Atmospheric pressure is very suitable at the lower operating temperatures. Process pressures in the range from about 0 to 150 psig are considered typical for preferred operations.

Following practice of the process of this invention the purified IPA may, if desired, be treated for further purification. Such further treatment(s) are suitably of conventional design and operation, typically involving distillation, azeotropic distillation, solvent extraction and/or extractive distillation. For example, the IPA recovered from practice of the invention can be subjected to extractive distillation with a water solvent to further separate diisopropyl ether overhead from a water and IPA rich bottoms product. Distillation of the IPA/water mixture then yields an azeotropic aqueous IPA solution (about 87% w IPA) overhead product while rejecting residual sulfur compounds and polymers. Dehydration of the IPA solution can be accomplished by azeotropic distillation in the presence of added diisopropyl ether. The resulting IPA/diisopropyl mixture can be distilled to produce a high quality IPA product.

Similarly, the upper nonpolar diisopropyl ether rich phase which phase separates in the second process step and is withdrawn from the process in the third process step can be treated according to procedures known and practiced in the art for recovery and purification of its valuable content of diisopropyl ether and IPA. Conventional propylene hydration processing facilities provide means for recovery and purification of diisopropyl ether byproduct from mixtures resulting from distillations involved in IPA finishing.

When practiced together with conventional distillative and/or extractive separations, the invention has advantage from the standpoint of producing a product of enhanced quality. This is particularly true for the preparation of low odor products suitable for use in cosmetics, pharmaceuticals, and the like. Practice of the invention in conjunction with conventional purification techniques also enables the processing of low quality propylene feedstocks into IPA products of acceptable quality. In general, it is recognized that the lower the quality of the propylene feed, the higher the content of polymeric and/or sulfur-containing impurities in the hydration process IPA product produced from the feed. By providing a means for purification of crude IPA independent of distillation and extractive distillation, the invention makes it possible to efficiently upgrade the performance of new or existing IPA finishing facilities.

Additionally, or alternatively, the invention can be applied to eliminate, at least in part, conventional requirements for distillation and/or extraction of the IPA. Advantage may then be realized, for instance, through reductions in the number of distillation operations, in the the size of distillation equipment, and in the energy requirements for vaporization and condensation of the distillation streams.

The invention is further described with reference to the following examples, which are intended to illustrate certain preferred embodiments without limiting its broader scope.

EXAMPLE 1

For the purpose of this example, reference is made to the simplified schematic flow diagram provided by the attached FIGURE. Numbers referenced to identify process streams and process equipment correspond to the designations shown on the drawing.

This example describes one embodiment of the application of a continuous process according to the invention to the purification of a crude IPA stream (designated by the reference number 10) containing 54.7% w IPA, 5.0% w diisopropyl ether, 0.2% w of polymers (i.e., $C_9$ and higher) and sulfur-containing impurities, 0.4% w acetone, and 39.7% w water. This stream has a total flowrate of 9,160 lbs. per hour. The higher carbon number "polymer" compounds are present at a level of about 18 lbs. per hour and sulfur-containing impurities at a level of about 4.5 ppm (parts per million by weight calculated on elemental sulfur).

In the first process step, the 9,160 lbs. per hour of this crude IPA is diluted with both water and isopropyl ether by mixing and diluting stream 10 with a stream 19, supplied from a source external to the finishing process, consisting of 20,807 lbs. per hour of water and with a stream 37 recycled from the upper phase of the second phase separation zone. Under steady state operation, stream 37 consists of 171 lbs. per hour of IPA, 290 lbs. per hour of diisopropyl ether, a trace of polymers and sulfur-containing impurities, 9 lbs. per hour of acetone, and 67 lbs. per hour of water. The resulting dilute crude IPA stream 11 then contains 5,179 lbs. per hour of IPA, 747 lbs. per hour of isopropyl ether, 25,115 lbs. per hour of water, and 18 lbs. per hour of polymers and sulfur-containing impurities.

Stream 11 (and all process flows downstream of 11) have a temperature of about 190° F. Process pressure varies from about 90 psig in stream 11 to about 75 psig in the product stream designated 31.

The dilute crude IPA mixture 11 is introduced into a first phase separation zone, in this embodiment a horizontal vessel designated 20, for continuous phase separation into first upper phase 24 and a first lower phase 25. The size of vessel 20 is about 2,400 gallons, providing an average residence time of about one hour, calculated on the total flow of stream 11. The first upper phase is continuously withdrawn from vessel 20 and from the process, as stream 26. Stream 26 carries with it about 17.7 lbs. per hour of the polymeric/sulfur-containing impurities, representing about 95% of the sulfur and about 98.5% of the polymers found in the crude IPA. Stream 26 additionally contains 611 lbs. per hour of diisopropyl ether, 376 lbs. per hour of IPA, 1 lb. per hour of acetone, and 146 lbs. per hour of water.

The first lower phase is continuously withdrawn from the first phase separation zone as stream 21, containing 4,803 lbs. per hour of IPA, 136 lbs. per hour of diisopropyl ether, 38 lbs. per hour of acetone, 24,968 lbs. per hour of water, and about 0.3 lbs. per hour of polymeric and sulfur-containing impurities.

Addition is made to stream 21 of 286 lbs. per hour of substantially pure isopropyl ether, introduced as stream 39, and the resulting mixture, stream 22, is introduced into the second phase separation zone, vessel 30. This vessel has a volume of 2,400 gallons and provides an average residence time of about one hour, calculated on total flow of stream 22. Phase separation in the second zone results in a second upper diisopropyl ether-rich phase 32 which is continuously withdrawn as stream 37 and recycled for dilution of the crude IPA upstream of the first phase separation zone. Stream 37 contains about 6.4 ppm of sulfur-containing compounds and a trace of polymer. The phase separation in the second zone also yields a second lower phase 33 which is continuously withdrawn as stream 31. This stream 31, representing the (partially) purified IPA product of the process, contains 4,633 lbs. per hour of IPA, 131 lbs. per hour of diisopropyl ether, 24,300 lbs. per hour of water, and only about 0.3 lbs. per hour of polymer and 0.07 ppm of sulfur-containing impurities.

Overall, practice of this embodiment of the process of the invention results in a highly effective reduction of the content in the IPA of both the diisopropyl ether and the polymeric and sulfur-containing impurities. Polymers have been reduced to a level of only about 1.5% w and sulfur to a level of only about 5% w, relative to their respective contents in the crude IPA stream 10. Composition of the primary crude IPA streams, both before and after treatment according to this embodiment of the invention, are summarized in the following Table 1.

TABLE 1

| Component | Stream 10 lb/hr | Stream 31 lb/hr |
|---|---|---|
| IPA | 5,008 | 4,633 |
| diisopropyl ether | 456 | 131 |
| polymers | 18 | 0.3 |
| sulfur compounds | 0.041 | 0.0022 |
| acetone | 39 | 37 |
| water | 3,639 | 24,300 |

EXAMPLE 2

A series of experiments were carried out to demonstrate the equilibrium phase distribution of polymeric components, typical of those generated in propylene hydration processes, in the two liquid phases which result from the phase separation of mixtures containing water, IPA, and diisopropyl ether in controlled proportions. The results of these experiments demonstrate the effectiveness of the removal of polymeric impurities from crude IPA streams in the course of this invention.

A control experiment ("no. 0") illustrates the analysis of a typical crude IPA product for polymeric impurities. (All polymer analyses given for these experiments were obtained by GLC separation on a boiling point capillary column.)

In experiment no. 1, 200 ml of typical crude IPA was mixed (shaken) with a 440 ml of water in a stoppered cylinder and the mixture placed in a constant temperature bath at a temperature of 30° C. After five minutes of phase separation, a sample of the lower (polar) phase was withdrawn and analyzed for content of polymeric impurities. This five-minute phase separation is represented as experiment no. 1. For experiment no. 2, the same mixture was allowed to continue to phase separate at 23° C. for an additional 225 minutes. Analysis was made of the polymeric impurities content of the lower phase after the continued phase separation.

In experiment no. 3, 200 ml of typical crude IPA was mixed with 440 ml of water and the mixture allowed to phase separate for 5 minutes at 60° C. For experiment no. 4, phase separation of this same mixture was continued for an additional 90 minutes at 40° C. In each case, a sample of the lower phase was withdrawn for determination of its polymer content.

Results of the experiments are presented in Table 2, in terms of the parts per million by weight (ppm) of polymeric impurities remaining in the IPA-rich polar lower phases resulting from the phase separations.

TABLE 2

| Experiment no. | Time | Temp. (C.) | ppm of polymer in polar phase | | | |
|---|---|---|---|---|---|---|
| | | | $C_9$-$C_{12}$ | $C_{12}$-$C_{15}$ | $C_{15}$-$C_{18}$ | $C_{18}^+$ |
| 0 (control) | 0 | — | 1831 | 24 | 4 | 107 |
| 1 | 5 min | 30 | 44 | 7 | 1 | 62 |
| 2 | 225 min | 23 | 11 | 0 | 0 | 25 |
| 3 | 5 min | 60 | 54 | 11 | 3 | 33 |
| 4 | 90 min | 40 | 11 | 0 | 1 | 25 |

We claim as our invention:

1. A process for the purification of a crude isopropyl alcohol product of propylene hydration, containing isopropyl alcohol, diisopropyl ether, and water, which comprises steps for:

(a) mixing the crude isopropyl alcohol product with the recycle stream from subsequent process step (f) and with added water in the amount required to provide a mixture containing between about 73 and 83% w water, (b) in a first phase separation step, phase separating the mixture from step (a) into a first upper (nonpolar) phase rich in diisopropyl ether and a first lower (polar) phase rich in isopropyl alcohol and water, (c) withdrawing the first upper phase from the process, (d) admixing the first lower phase with added diisopropyl ether to obtain a mixture containing between about 10 and 21% w isopropyl alcohol, between about 1 and 4% w diisopropyl ether, and between about 77 and 87% w water, relative to the total weight of the resulting mixture,
(e) in a second phase separation step, phase separating the mixture from step (d) into a second upper (nonpolar) phase rich in diisopropyl ether and a second lower (polar) phase rich in isopropyl alcohol and water,
(f) recycling the second upper phase for use in dilution of the crude isopropyl and alcohol product in step (a), and
(g) recovering the second lower phase as a purified isopropyl alcohol product.

2. The process of claim 1, wherein the crude isopropyl alcohol product contains between about 40 and 70% w of isopropyl alcohol, and at least about 1% w of diisopropyl ether.

3. The process of claim 2, wherein the crude isopropyl alcohol product contains between about 1 and 10% w of diisopropyl ether.

4. The process of claim 3, wherein the crude isopropyl alcohol product contains between about 20 and 55% w water.

5. The process of claim 4, wherein the temperature in each of the two phase separation steps is in the range from about 15 to 150C.

6. The process of claim 5, wherein the temperature in each of the two phase separation steps is in the range from about 50 to 110C.

7. The process of claim 1, wherein the temperature in each of the two phase separation steps is in the range from about 50 to 110C.

8. The process of claim 6, wherein the crude isopropyl alcohol product contains between about 0.1 and 2.0% w of polymeric and sulfur impurities.

9. The process of claim 1, wherein the crude isopropyl alcohol product contains between about 0.1 and 2.0% w of polymeric and sulfur impurities.

* * * * *